United States Patent [19]

Fuchs et al.

[11] Patent Number: 4,992,589
[45] Date of Patent: Feb. 12, 1991

[54] SUBSTITUTED PHENYL HYDROXYETHYL SULFONES, AND PROCESS FOR THEIR PREPARATION

[75] Inventors: Hermann Fuchs, Königstein/Taunus; Theodor Papenfuhs, Frankfurt am Main; Werner Brodt, Hattersheim am Main; Folker Kohlhaas, Hochheim am Main, all of Fed. Rep. of Germany

[73] Assignee: Hoechst Aktiengesellschaft, Frankfurt am Main, Fed. Rep. of Germany

[21] Appl. No.: 231,655

[22] Filed: Aug. 10, 1988

Related U.S. Application Data

[63] Continuation of Ser. No. 65,295, Jun. 22, 1987, abandoned, which is a continuation of Ser. No. 756,771, Jul. 18, 1985, abandoned.

[30] Foreign Application Priority Data

Jul. 20, 1984 [DE] Fed. Rep. of Germany ....... 3426729
Jan. 30, 1985 [DE] Fed. Rep. of Germany ....... 3502991

[51] Int. Cl.$^5$ .................. C07C 317/14; C07C 321/28
[52] U.S. Cl. .................................... 564/440; 534/642; 568/22; 568/30; 558/389; 562/37; 562/41; 562/58; 562/61; 562/66; 562/67; 564/99; 564/194; 564/299; 564/430; 564/433; 564/434
[58] Field of Search ............... 564/430, 433, 434, 440; 534/642

[56] References Cited

U.S. PATENT DOCUMENTS

3,629,330 12/1971 Brody et al. ........................ 564/440
3,636,064 1/1972 Hotta et al. ......................... 564/440
4,577,015 3/1986 Jager et al. ............................ 544/76

OTHER PUBLICATIONS

Text. Chem. Color 19, 25-28 (1987).
JSDC, 103, 100-105 (1987).
A. N. Derhushire et al, JSDC 96, 570-575 (1980).

Primary Examiner—Glennon H. Hollrah
Assistant Examiner—Brian M. Burn

[57] ABSTRACT

Compounds of the formula (1)

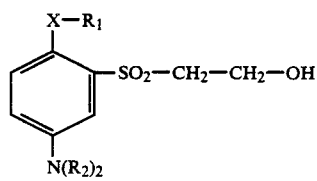

in which X denotes a sulfur atom or the group

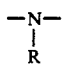

in which R denotes a hydrogen atom, an alkylene-$C_1$-$C_4$-alkoxy-$C_1$-$C_6$- or alkyl-$C_1$-$C_6$- group, each of which can be substituted by hydroxyl, sulfo, carboxyl or cyano groups, $R_1$ denotes a hydrogen atom or an alkyl-$C_1$-$C_6$-group which can be substituted by —$SO_3M$ or COOM groups (where M denotes an H, Li, Na, K or Ca atom), hydroxyl, amino, methylamino, acetylamino, alkyl-$C_1$-$C_4$-sulfonylamino, methoxy, ethoxy, β-hydroxyethylsulfonyl, phenyl, monosulfophenyl, disulfophenyl, or 4-[β-hydroxyethylsulfonyl]-2-sulfophenyl groups, or represents a phenyl or naphthyl group, each of which can be substituted by —$SO_3M$ or COOM groups (where M denotes an H, Li, Na, K or Ca atom), alkyl-$C_1$-$C_4$-, alkoxy-$C_1$-$C_4$-, amino, methylamino, alkyl-$C_1$-$C_4$-sulfonylamino or acetylamino groups, and $R_2$ is hydrogen or oxygen, and process for their preparation by reacting compounds of the formula (2)

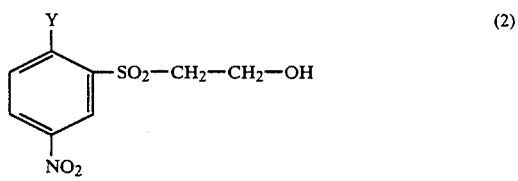

in which Y denotes a chlorine or bromine atom, with a compound of the formula (3)

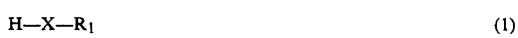

in which X and $R_1$ have the stated meanings, at between 20° and 90° C in a solvent which is suitable in respect of the reactants of the formulae (2) and (3) and in the presence of an acid-binding agent to give compounds of the formula (4)

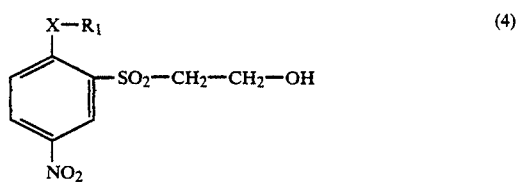

in which X and $R_1$ have the stated meanings, and if desired using these compounds in a manner known per se to compounds of the formula (1) where $R_2$=H.

1 Claim, No Drawings

SUBSTITUTED PHENYL HYDROXYETHYL SULFONES, AND PROCESS FOR THEIR PREPARATION

This application is a continuation of our copending application Ser. No. 07/065,295, filed 6/22/87, now abandoned, which is a continuation of Ser. No. 06/756,771, filed 7/18/85, also abandoned.

The present invention relates to new substituted phenyl hydroxyethyl sulfones of the general formula (1)

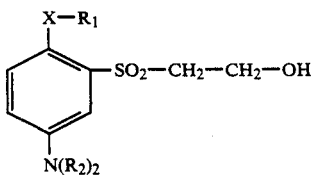  (1)

in which X denotes a sulfur atom or the group

in which R denotes a hydrogen atom, an alkylene-$C_1$-$C_4$ alkoxy-$C_1$-$C_6$- or alkyl$C_1$-$C_6$-group, each of which can be substituted by hydroxyl, sulfo, carboxyl or cyano groups, $R_1$ denotes a hydrogen atom or an alkyl-$C_1$-$C_6$-group which can be substituted by —$SO_3M$ or COOM groups (where M denotes an H, Li, Na, K or Ca/2 atom), hydroxyl, amino, methylamino, acetylamino, alkyl-$C_1$-$C_4$-sulfonylamino, methoxy, ethoxy, β-hydroxyethylsulfonyl, phenyl, monosulfophenyl, disulfophenyl, or 4-[β-hydroxyethylsulfonyl]-2-sulfophenyl groups, or represents a phenyl or naphthyl group, each of which can be substituted by —$SO_3M$ or COOM groups (where M denotes an H, Li, Na, K or Ca/2 atom), alkyl-$C_1$-$C_4$-, alkoxy-$C_1$-$C_4$-, amino, methylamino, alkyl-$C_1$-$C_4$-sulfonylamino or acetylamino groups, and $R_2$ denotes a hydrogen or oxygen atom, and to a process for their preparation in which compounds of the general formula (2)

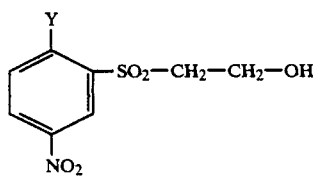  (2)

in which Y denotes a chlorine or bromine atom, are reacted with a compound of the general formula (3)

  (3)

in which X and $R_1$ have the abovementioned meanings, at temperatures between 20° and 90° C, preferably between 40° and 70° C, in a solvent which is suitable in respect of the reactants of the stated formula (2) and (3) and in the presence of an acid-binding agent to give compounds of the general formula (4)

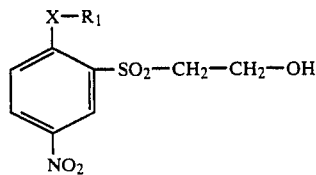  (4)

in which X and $R_1$ have the abovementioned meanings, and if desired these compounds are reduced in a manner known per se to the compounds of the stated formula (1) where $R_2$=H.

Specific examples of compounds of the stated general formula (3) are the compounds of the following formulae:

HS—$CH_2$—$CH_2$—OH
$NH_3$
$H_2N$—$CH_3$
$H_2N$—$CH_2$—$CH_2$—$CH_2$—$CH_2$—$CH_2$—$CH_3$

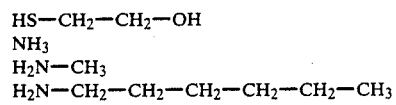

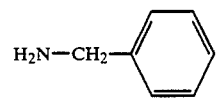

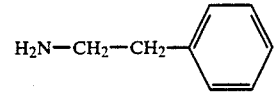

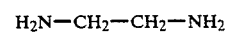

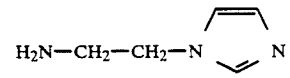

$H_2N$—$CH_2$—$CH_2$—OH
$H_2N$—$CH_2$—$CH(CH_3)$—OH
$H_2N$—$CH(CH_3)$—$CH_2$—OH
$H_2N$—$CH_2$—$CH_2$—$CH_2$—$CH_2$—OH
$H_2N$—$CH_2$—$CH_2$—$CH_2$—$CH_2$—$CH_2$—$CH_2$—$NH_2$
$H_2N$—$CH(C_3H_7)$—$CH(CH_3)$—OH
$H_2N$—$CH_2CH_2$—O—$(CH_2CH_2)_n$—OH n = 1-3
$H_2N$—$CH_2$—$CH_2$—$OCH_3$
$H_2N$—$CH_2$—$CH_2$—$OC_2H_5$
$H_2N$—$CH_2$—$CH_2$—NH—CO—$CH_3$
$H_2N$—$CH_2$—$CH_2$—$CH_2$—NH—$CH_3$
$H_2N$—$CH_2CH_2$—NH—$(CH_2CH_2$—$O)_n$H n = 1-3
$H_2N$—$CH_2CH_2$—$N(CH_2CH_2OH)_2$
$H_2N$—$CH_2$—$CH_2$—$SO_2$—$CH_2$—$CH_2$—OH
$H_2N$—$CH_2CH_2$—NH—$SO_2CH_2CH_2$—$OSO_3H$
$H_2N$—$CH_2$—COOH
$H_2N$—$CH(CH_3)$—COOH
$H_2N$—CH(COOH)—$CH_2$—$SO_3H$
$H_2N$—$CH_2$—$CH(SO_3H)$—COOH

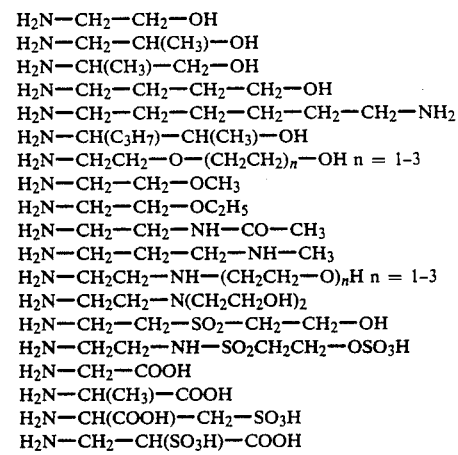

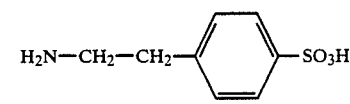

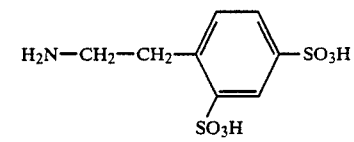

-continued

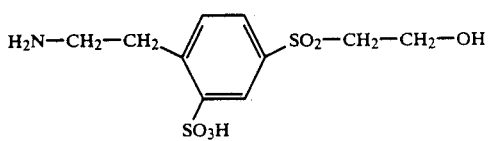

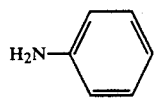

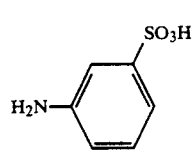

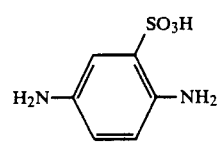

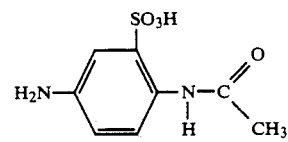

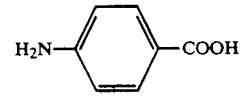

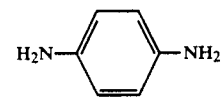

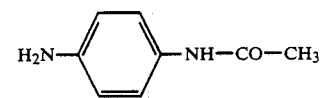

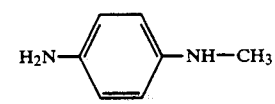

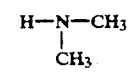

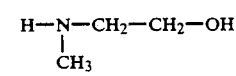

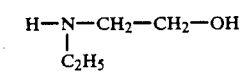

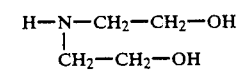

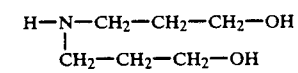

-continued

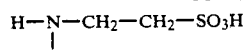

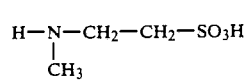

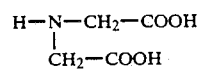

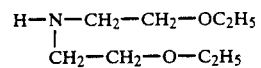

Since hydrogen chloride or bromide is eliminated in the first stage of the reaction, it is necessary to work in the presence of an acid-binding agent. Suitable for this purpose are not only inorganic compounds, such as, for example, sodium hydroxide, potassium hydroxide, sodium carbonate, potassium carbonate, sodium acetate or potassium acetate, but also organic basic compounds, such as, for example, trialkyl-$C_1$-$C_4$-amines, such as, for example, trimethylamine or triethylamine, or pyridine, quinoline, picoline or morpholine. In each case the acid-binding agent needs to be present in an at least equivalent amount relative to the monochloro or monobromo compound of the formula (2). If the reactant of the formula (3) is a compound with a basic reaction, such as, for example, ethanolamine or ethylenediamine, and if said compound is used in sufficient excess, this compound acts as an acid acceptor, thereby dispensing with the need to add a separate inorganic or organic acid-binding agent.

Examples of suitable solvents which can serve as the reaction medium in the first state of the reaction are water, alkanols, of 1 to 4 carbon atoms, such as, for example, methanol, ethanol, propanol or isobutanol, dioxane, toluene, xylenes, chlorobenzene, o-dichlorobenzene, m-dichlorobenzene, dimethylformamide and N-methylpyrrolidone. If one or both of the two reactants of the formulae (2) and (3) is not completely soluble in the solvent used, such as, for example, in mercaptoethanol, the reaction will partly take place in suspension without detriment.

However, it is also possible to use the reactant of the stated formula (3) as the solvent by using it in sufficient excess.

If use is made of a solvent in which each of the two reactants is completely soluble, it is advisable to react 1 mol of the compound of the formula (2) with 1–2.5 mol of a compound of the formula (3). It is admittedly possible to use a great excess of a compound of the formula (3), but this does not yield any further benefit, and therefore is not advisable.

If use is made of a solvent in which one or both of the reactants of the formulae (2) and (3) is not completely soluble, or if use is made of excess reactant of the formula (3) as a solvent, it is advisable to react 1 mol of the compound of the formula (2) with 1–4 mol of the compound of the formula (3). In this case it is likewise possible to use a greater excess of the compound of the formula (3), but it is not advisable.

The nitro compound of the formula (4) can be isolated from the reaction mixture most simply by crystallization and subsequent filtration, if necessary after cooling down. The isolation can also be effected in similar manner by distilling off the solvent or the excess reagent of the formula (3), which can in this way be advantageously recovered for further reactions. Subsequently the concentrated reaction mixture is stirred into cold water which may contain a salt, such as, for example, NaCl, KCl or Na$_2$SO$_4$. The product which crystallizes out in the course of the stirring can be isolated by filtration, if necessary after acidification with mineral acid.

The resulting compounds of the general formula (4) can be subsequently reduced to the corresponding amino compounds of the formula (1) where R$_2$=H. This reduction can be carried out in a manner known per se, by catalytic hydrogenation with hydrogen using known catalyts, such as palladium, platinum or Raney nickel, at temperatures between 20° and 150° C, preferably between 50° and 110° C, and elevated pressure, for example between 30 and 100 bar, preferably between 40 and 55 bar, or by Bechamp reduction with iron in an acid or alkaline medium, preferably in an acid medium, for example using iron in ethanol/glacial acetic acid.

Particularly advantageously the process according to the invention is carried out by subjecting the reaction solution of the chlorine exchange reaction (1st reaction stage) without intermediate isolation of the compounds of the formula (4) directly to catalytic hydrogenation. In this way it is possible to reduce energy and effluent costs.

The reduction, irrespective of whether it is a catalytic reduction or a Bechamp reduction, is advantageously carried out in a suitable solvent, such as water, methanol or ethanol, or in a mixture of water and methanol on the one hand or water and ethanol on the other, since in this form of the reduction the target products (compounds of the formula (1) where R$_2$=H) can be made to crystallize in a simple manner by cooling down, if necessary after acidification with mineral acid, as a free amino compound or in the form of the mineral acid salt and be isolated by subsequent filtration.

The mother liquors can be recycled for subsequent hydrogenation batches. Similarly, the organic solvent can be recovered from the mother liquor by simple distillation under atmospheric pressure.

Using the process according to the invention it is possible to obtain the new compounds of the formula (1) in high to very high yields. Furthermore, according to the invention the compounds of the formula (1) can be invariably obtained in high purity in the case of R$_2$=O and in the case of R$_2$=H if produced in crystalline form during the reduction, and moreover the effluent is only slightly polluted with inorganic salts.

The new compounds of the stated general formula (1) which can be obtained according to the invention are valuable intermediates for preparing fiber-reactive azo and dioxazine dyestuffs. To prepare these dyestuffs, first the compounds of the general formula (1) (R$_2$=H) are reacted with chloranil and then oxidative ring closure and subsequent esterification with oleum gives dyestuffs of the formula A dyestuff of this general formula where —XR$_1$=—NH—CH$_2$—CH$_2$—OSO$_3$H produces pure blue dyeings on cotton.

EXAMPLE 1

(a) (2-β-Hydroxyethylamino-5-nitrophenyl hydroxyethyl sulfone)

132.85 g of 2-chloro-5-nitrophenyl hydroxyethyl sulfone are added at 65° C. to a solution of 76.5 g of ethanolamine in 500 ml of methanol in the course of 15 minutes, and the mixture is stirred at this temperature for 6 hours. After the reaction has ended, 400 ml of methanol are distilled off with continuous addition of water. As the reaction solution cools down the product crystallizes out and is isolated by filtration; the solvent which has been distilled off is used for subsequent reactions. The result obtained is 135 g of 2-β-hydroxyethylamino-5-nitrophenyl hydroxyethyl sulfone (purity 99%) as a yellow solid having a melting point of 130°-132° C., which corresponds to a yield of 93% of theory, relative to starting 2-chloro-5-nitrophenyl hydroxyethyl sulfone.

(b) (5-Amino-2-β-hydroxyethylaminophenyl hydroxyethyl sulfone)

To carry out a catalytic hydrogenation on the 2-β-hydroxyethylamino-5-nitrophenyl hydroxyethyl sulfone obtained in section a), 116 g of this product are hydrogenated at 100° C and 50 bar of hydrogen in 800 ml of methanol using a nickel catalyst. After the catalyst has been filtered off, the product is crystallized by cooling down and isolated by filtration. This gives 90.4 g of 5-amino-2-β-hydroxyethylaminophenyl hydroxyethyl sulfone having a melting point of 136°-138° C and a purity of >96%, which corresponds to a yield of 83.5% of theory, relative to starting 2-β-hydroxyethylamino-5-nitrophenyl hydroxyethyl sulfone.

EXAMPLE 2

Example 1 is repeated, except that the product is not isolated after the 1st reaction step, affording, after catalytic hydrogenation under the conditions of Example 1(b), 109.3 g of 5-amino-2-β-hydroxyethylaminophenyl hydroxyethyl sulfone having a melting point of 135°-138° C., which corresponds to a yield of 84% of theory, relative to starting 2-chloro-5-nitrophenyl hydroxyethyl sulfone.

EXAMPLE 3

(a) (2-β-Aminoethylamino-5-nitrophenyl hydroxyethyl sulfone)

132.85 g of 2-chloro-5-nitrophenyl hydroxyethyl sulfone are added at 65°-70° C with stirring to 250 g of 1,2-diaminoethane in the course of 15 minutes, and the mixture is stirred at this temperature for a further 15 minutes. The reaction mixture is then allowed to cool down to room temperature with stirring and is poured onto 1 l of ice-water, and the product is isolated by

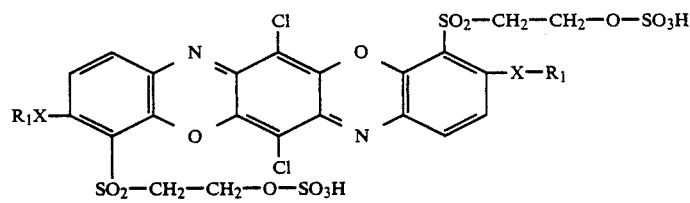

filtration. This gives 139.6 g (2-β-aminoethylamino)-5-nitrophenyl hydroxyethyl sulfone having a melting point of 147° C and a purity of >98%, which corresponds to a yield of 94.5% of theory, relative to starting 2-chloro-5-nitrophenyl hydroxyethyl sulfone.

(b) (5-Amino-2-β-aminoethylaminophenyl hydroxyethyl sulfone)

If the compound obtained in section (a) is hydrogenated catalytically as described in Example 7(b), this gives 77.5 g of 5-amino-2-β-aminoethylaminophenyl hydroxyethyl sulfone. By treatment with methanolic hydrochloric acid it is possible to isolate the product in crystalline form as a hydrochloride having a melting point of 242° C

EXAMPLE 4

(2-β-Hydroxyethylmercapto-5-nitrophenyl hydroxyethyl sulfone)

58.75 g of potassium carbonate are added at 22° C to a suspension of 132.85 g of 2-chloro-5-nitrophenyl hydroxyethyl sulfone in 100 ml of water and 80 g of 2-mercaptoethanol in the course of 1.5 hours, and the mixture is stirred at room temperature for 4 hours. The reaction mixture is then filtrated with suction, and the filter residue is washed with water until neutral. Drying these gives 124.3 g of 2-β-hydroxyethylmercapto-5-nitrophenyl hydroxyethyl sulfone having a melting point of 116°-118° C (purity about 99%), which corresponds to a yield of 81% of theory, relative to starting 2-chloro-5-nitrophenyl hydroxyethyl sulfone.

EXAMPLE 5

(a) (2-Phenethylamino-5-nitrophenyl hydroxyethyl sulfone)

132.85 g of 2-chloro-5-nitrophenyl hydroxyethyl sulfone are added at 60° C to a solution of 151.3 g of phenethylamine in 500 ml of isopropanol, and the temperature is then raised to 84° C. The mixture is stirred at this temperature for 1 hour and is then allowed to cool down. The product is crystallized by pouring the reaction solution into ice-water and is isolated by filtration. This gives 163.1 g of 2-phenethylamino-5-nitrophenyl hydroxyethyl sulfone having a melting point of 95°-95.5° C and a purity of 99.5%. This corresponds to a yield of 93% of theory, relative to starting 2-chloro-5-nitrophenyl hydroxyethyl sulfone.

(b) (5-Amino-2-phenethylaminophenyl hydroxyethyl sulfone)

If the compound obtained in section (a) is hydrogenated catalytically as described in Example 7(b), this gives 162.0 g of 5-amino-2-phenethylaminophenyl hydroxyethyl sulfone in the form of a hydrochloride of melting point of 197° C. The purity is 98% corresponding to a yield of 89% of theory, relative to starting 2-phenethylamino-5-nitrophenyl hydroxyethyl sulfone.

EXAMPLE 6

(2-(4-Aminophenylamino)-5-nitrophenyl hydroxyethyl sulfone)

132.85 g of 2-chloro-5-nitrophenyl hydroxyethyl sulfone are added at 65° C under nitrogen to a solution of 118.8 g of 1,4-phenylenediamine in 500 ml of methanol in the course of 30 minutes. The reaction solution is stirred at this temperature for a further 4 hours and is then allowed to cool down to room temperature, and the reaction product is crystallized by addition of 1 l of ice-water. Filtering with suction and drying gives 168 g of 2-(4-aminophenylamino)-5-nitrophenyl hydroxyethyl sulfone having a melting point of 147°-149° C and a purity of >99%, which corresponds to a yield of 99% of theory, relative to starting 2-chloro-5-nitrophenyl hydroxyethyl sulfone.

EXAMPLE 7

(a) (2-Amino-5-nitrophenyl hydroxyethyl sulfone)

132.85 g of 2-chloro-5-nitrophenyl hydroxyethyl sulfone in 650 ml of i-propanol are heated in the presence of 41.25 g of gaseous ammonia to 130° C for 2 hours in an autoclave. After cooling down to room temperature the solution is poured onto 1000 ml of water, and the product which crystallizes out on cooling to 0° C. is isolated by filtration. This gives 118.2 g of 2-amino-5-nitrophenyl hydroxyethyl sulfone having a melting point of 175° C. and a purity of >99%, which corresponds to a yield of 94% of theory, relative to starting 2-chloro-5-nitrophenyl hydroxyethyl sulfone.

(b) (2,5-Diaminophenyl hydroxyethyl sulfone)

The compound obtained in section (a) is dissolved in 400 ml of methanol and is catalytically hydrogenated at 60° C. and 40 bar of hydrogen using a palladium catalyst. Filtering off the catalyst and distilling off the solvent gives 99.5 g of 2,5-diaminophenyl hydroxyethyl sulfone as a dark brown oil. By treatment with methanolic hydrochloric acid the product can be isolated in a crystalline form as a hydrochloride having a melting point of 254.5° C.

EXAMPLE 8

(a) (2-Mercaptoethyl-5-nitrophenyl hydroxyethyl sulfone)

132.85 g of 2-chloro-5-nitrophenyl hydroxyethyl sulfone are suspended together with 69.1 g of potassium carbonate in 500 ml of ethylmercaptan, and the reaction is allowed to proceed at 30° C. for 2 hours. The ethylmercaptan excess is distilled off under a high vacuum, the residue is taken up in ethanol, and the product is crystallized by pouring into ice-water. After filtration this gives 140.5 g of 2-mercaptoethyl-5-nitrophenyl hydroxyethyl sulfone having a melting of 112°-114° C (purity >95%), which corresponds to a yield of 91.5% of theory, relative to starting 2-chloro-5-nitrophenyl hydroxyethyl sulfone.

(b) (5-Amino-2-Mercaptoethylphenyl hydroxyethyl sulfone)

If 118 g of the compound obtained in section (a) are hydrogenated as described in Example 7(b), this gives 92.4 g of 5-amino-2-mercaptoethylphenyl hydroxyethyl sulfone in the form of a yellow oil. By treatment with methanolic hydrochloric acid it is possible to isolate the product in crystalline form as a hydrochloride having a melting point of >330° C.

EXAMPLE 9

(5-amino-2-(methyl-2'-sulfoethyl)aminophenyl hydroxyethyl sulfone)

132.85 g of 2-chloro-5-nitrophenyl hydroxyethyl sulfone are added at 65° C to a suspension of 201 g of the sodium salt of N-methyltaurine in 500 ml of methanol in the course of 15 minutes, and the mixture is stirred under reflux for 4 hours. After cooling down to room temperature the reaction mixture is transferred into an autoclave and is subjected to a catalytic reduction with Raney nickel at 40° C and a hydrogen pressure of 40 bar. After cooling down to room temperature, 102 ml of 30.5% strength hydrochloride acid are added, and the product is crystallized out in an ice bath. Filtering with suction and drying gives 142.5 g of 5-amino-2-(methyl-2'-sulfoethyl)-aminophenyl hydroxyethyl sulfone having a melting point of 214° C (decomposition) and a purity of 94%, which corresponds to a yield of 89.5% of theory, relative to starting 2-chloro-5-nitrophenyl hydroxyethyl sulfone.

EXAMPLE 10

(a) (2-γ-Hydroxypropylamino-5-nitrophenyl hydroxyethyl sulfone)

132.85 g of 2-chloro-5-nitrophenyl hydroxyethyl sulfone are added at 65° C to a solution of 93.8 g of 3-aminopropan-1-ol in 500 ml of methanol in the course of 15 minutes, the solution is stirred at this temperature for 3 hours, the bulk of the solvent is distilled off with the simultaneous addition of 400 ml of water, the residue is cooled down to 0° C, and the product which crystallizes out in the course of the cooling is isolated by filtration. This gives 137 g of 2-γ-hydroxypropylamino-5-nitrophenyl hydroxyethyl sulfone in the form of a yellow solid having a melting point of 75°–77° C and a purity of 98%, which corresponds to a yield of 88% of theory, relative to starting 2-chloro-5-nitrophenyl hydroxyethyl sulfone.

(b) (5-Amino-2-γ-hydroxypropylaminophenyl hydroxyethyl sulfone)

If the compound obtained in section (a) is hydrogenated as described in Example 7(b), this gives 94.1 g of 5-amino-2-(γ-hydroxyphenyl)aminophenyl hydroxyethyl sulfone having a melting point of 100°–101.5° C and a purity of 95%, which corresponds to a yield of 65% of theory, relative to starting 2-chloro-5-nitrophenyl hydroxyethyl sulfone.

EXAMPLE 11

(a) (2-[2-(4-Morpholinyl)-ethyl]-amino-5-nitrophenyl hydroxyethyl sulfone)

132.85 g of 2-chloro-5-nitrophenyl hydroxyethyl sulfone are added at 50° C to a solution of 143.3 g of 2-(4-morpholinyl)-ethylamine in 500 ml of isopropanol in the course of 15 minutes, and the mixture is subsequently stirred at 70° C for 2 hours. After cooling down, the reaction mixture is poured onto 1500 ml of ice-water. The product crystallizes out and is isolated by filtration. This gives 169.8 g of (2-[2-(4-morpholinyl)-ethyl]-amino-5-nitrophenyl hydroxyethyl sulfone having a melting point of 100°–101° C. and a purity of >99.5% (HPLC), which corresponds to a yield of 94% of theory, relative to starting 2-chloro-5-nitrophenyl hydroxyethyl sulfone.

(b) (5-Amino-2-[2-(4-morpholinyl)-ethyl]-aminophenyl hydroxyethylsulfone)

The compound obtained in section (a) is catalytically hydrogenated at 40° C and 50 bar of hydrogen in 1000 ml of methanol. Filtering off the catalyst and distilling off the solvent leaves 157.7 g of 5-amino-2-[2-(4-morpholinyl)-ethyl]-aminophenyl hydroxyethyl sulfone in the form of a dark brown oil having a purity of 99.5% (HPLC), corresponding to a yield of 95.5%, relative to starting nitro compound.

MS[DCI(NH$_3$)]: m/z=347(M+NH$_4$+).

EXAMPLE 12

(a) (2-Morpholinyl-5-nitrophenyl hydroxyethyl sulfone)

132.85 g of 2-chloro-5-nitrophenyl hydroxyethyl sulfone are added at 60° C. to a solution of 108 g of morpholine in 500 ml of isobutanol in the course of 25 minutes, and the reaction mixture is then stirred at 75° C for 1 hour. The reaction mixture is allowed to cool down and is then poured onto 1500 ml of ice-water. The reaction product crystallizes out and is isolated by filtration. This gives 152 g of 2-morpholinyl-5-nitrophenyl hydroxyethyl sulfone having melting point of 155°–6° C and a purity of >99.7% (HPLC), which corresponds to a yield of 96% of theory, relative to starting 2-chloro-5-nitrophenyl hydroxyethyl sulfone.

MS:[DCI(NH$_3$)]: m/z 317(MH+).

(b) 5-Amino-2-morpholinylphenyl hydroxyethyl sulfone)

The compound obtained in section (a) is dissolved in 500 ml of methanol and is catalytically hydrogenated at 85° C and 50 bar of hydrogen. After filtering the catalyst off from the still hot reaction solution the product is allowed to crystallize out in an ice bath. This gives 123 g of 5-amino-2-morpholinylphenyl hydroxyethyl sulfone having a melting point of 203°–204° C. The purity is 99% (HPLC), corresponding to a yield of 85.1% of theory, relative to starting 2-morpholinyl-5-nitrophenyl hydroxyethyl sulfone.

MS:[DCI (NH$_3$)]: m/z=304(M+NH$_4$(+)).

EXAMPLE 13

(2-[2-(2'-hydroxyethoxy)-ethylamino]-5-nitrophenyl hydroxyethyl sulfone)

132.85 g of 2-chloro-5-nitrophenyl hydroxyethyl sulfone are added at 50° C to a solution of 115.5 g of 2,2'-aminoethoxyethanol in 500 ml of methanol in the course of 20 minutes, and the reaction mixture is then stirred at 65° C for 4 hours. After cooling down, the reaction mixture is poured onto 1500 ml of ice-water. The reaction product is allowed to crystallize out and is filtered off. This gives 155.3 g of 2-[2-(2'-hydroxyethoxy)-ethylamino]-5-nitrophenyl hydroxyethyl sulfone having a melting point of 86°–87° C and a purity of 99% (HPLC), which corresponds to a yield of 92% of theory, relative to starting 2-chloro-5-nitrophenyl hydroxyethyl sulfone.

Elemental analysis: Calculated: C 43.1, H 5.4, N 8.4, S 9.6. Found: C 43.0, H 5.5, N 8.5, S 9.1. $C_{12}H_{18}N_2SO_7$ (334.35).

EXAMPLE 14

(a) Anil condensation 260 g of 5-amino-2-β-hydroxyethylaminophenyl hydroxyethyl sulfone, 57.5 g of magnesium oxide and 124.1 g of 2,3,5,6-tetrachloro-1,4-benzoquinone (chloranil) are suspended in 1500 g of water, and the suspension is heated to 65° C and is stirred at 65° C for 2-5 hours. It is cooled down to 20° C, and the dark brown reaction product is filtered off. After washing with water the isolated anil of the formula

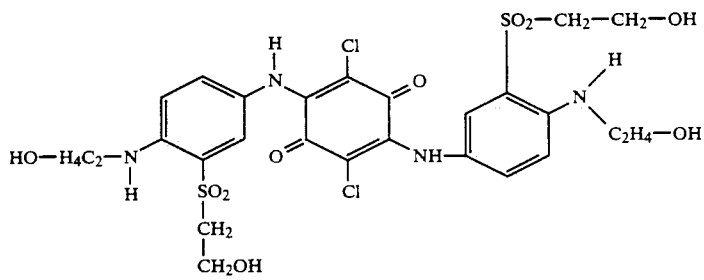

is dried at 60° C in vacuo.

(b) Ring closure and esterification 693 g of the anil obtained as described above are added to 7500 g of oleum (20% of SO₃) at such a rate that the temperature remains at 18°-22° C. Solution is obtained by stirring for 1 to 3 hours. 481 g of sodium peroxodisulfate are then added at such a rate that the temperature remains at 20°-23° C. The mixture is stirred for 15 hours and is then poured onto ice, the aqueous mixture is brought to pH 1 to 1.5 with calcium carbonate and then to pH 6 with sodium carbonate. The resulting gypsum is filtered off and is washed out with water.

The filtrate is evaporated to dryness. This gives a dyestuff of the formula

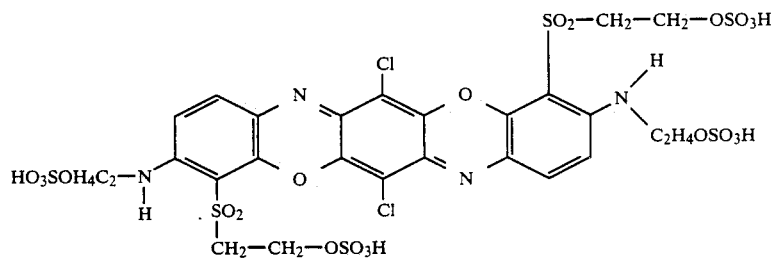

which produces pure blue dyeings on cotton.

We claim:

1. A compound of the formula:

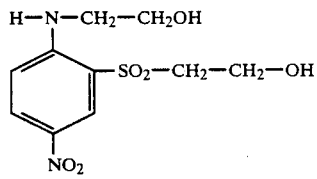

* * * * *